United States Patent
Lipson

(10) Patent No.: US 7,277,210 B2
(45) Date of Patent: Oct. 2, 2007

(54) MEASURING SPECTRAL LINES FROM AN ANALYTE USING MULTIPLEXED HOLOGRAMS AND POLARIZATION MANIPULATION

(75) Inventor: Jan Lipson, Cupertino, CA (US)

(73) Assignee: C8 Medisensors Inc., San Jose, CA (US)

( * ) Notice: Subject to any disclaimer, the term of this patent is extended or adjusted under 35 U.S.C. 154(b) by 284 days.

(21) Appl. No.: 11/187,350

(22) Filed: Jul. 21, 2005

(65) Prior Publication Data

US 2007/0019262 A1    Jan. 25, 2007

(51) Int. Cl.
G02B 5/32 (2006.01)
(52) U.S. Cl. .................. 359/15; 359/494; 385/24; 600/317; 356/320
(58) Field of Classification Search .................. 359/15, 359/494, 496; 385/11, 24; 600/317, 365; 356/319, 320
See application file for complete search history.

(56) References Cited

U.S. PATENT DOCUMENTS

| | | | | |
|---|---|---|---|---|
| 5,153,670 A | * | 10/1992 | Jannson et al. | 356/301 |
| 6,181,957 B1 | * | 1/2001 | Lambert et al. | 600/319 |
| 6,542,134 B1 | | 4/2003 | Raj | |
| 7,106,512 B2 | * | 9/2006 | Helbing et al. | 359/566 |
| 2003/0039437 A1 | * | 2/2003 | Boord et al. | 385/24 |
| 2004/0021920 A1 | * | 2/2004 | Psaltis | 359/15 |
| 2004/0033010 A1 | * | 2/2004 | McGuire, Jr. | 385/16 |
| 2005/0248819 A1 | * | 11/2005 | Hymel et al. | 359/15 |
| 2005/0248820 A1 | * | 11/2005 | Moser et al. | 359/15 |
| 2006/0092489 A1 | * | 5/2006 | Ingwall et al. | 359/15 |

OTHER PUBLICATIONS

PCT International Search Report and Written Opinion, PCT/US05/26039, Dec. 5, 2006, 7 pages.

* cited by examiner

Primary Examiner—Leonidas Boutsikaris
(74) Attorney, Agent, or Firm—Fenwick & West LLP

(57) ABSTRACT

An optical apparatus in which multiplexed holograms are used to achieve wavelength selectivity and polarization manipulation is used to facilitate near-normal incidence of light on the holograms. The polarization manipulation allows light reflected from the holograms to be separated from the light incident on the holograms. In one application, the apparatus can be used to extract spectral lines of an analyte from radiation scattered from a sample.

49 Claims, 9 Drawing Sheets

MEASURING SPECTRAL LINES FROM AN ANALYTE USING MULTIPLEXED HOLOGRAMS AND POLARIZATION MANIPULATION

CROSS-REFERENCE TO RELATED APPLICATION

This application claims priority under 35 U.S.C. § 119(e) to U.S. Provisional Patent Application Ser. No. 60/590,413, "Compact and Highly Efficient Apparatus to Measure Spectral Lines from an Analyte with a Wide Field of View," filed Jul. 22, 2004 by Jan Lipson. The subject matter of all of the foregoing is incorporated herein by reference in their entirety.

BACKGROUND OF THE INVENTION

1. The Field of the Invention

This invention relates generally to measuring analytes in samples based on an electromagnetic spectrum that is characteristic of the analyte and, more specifically, doing so by use of multiplexed holograms and polarization manipulation.

2. Background and Relevant Art

Many attempts have been made to create appropriate apparatus for the non-invasive measurement of significant substances within biological organisms. The importance of such measurement capability arises not only from the need to observe biochemical reactions in such organisms without disturbance to the system but also in order to help control chronic diseases such as diabetes, where it is highly desirable to measure the patients blood glucose levels much more frequently than is practical, when puncturing the skin is required.

Spectroscopy has been proposed to make such measurements. An important consideration in the design of spectrometers is the field of view of the apparatus for a given resolution. In particular, it is often advantageous to use a large detector so as to image a larger volume of the sample. However, it is generally undesirable to increase the diameter of the collecting optics in proportion. Therefore, it is usually desirable to have as large a field of view as possible as a fraction of the diameter of the collection optics.

U.S. Pat. No. 5,768,040 presents a spectrometer arrangement which as a composite has a wide field of view. The apparatus is composed of multiple spectrometers, each of which is based on spherical convex holographic diffraction gratings and associated reflection optics. The cost of the whole apparatus is comprised of a multiplicity of these spectrometers and is prohibitive for many applications. In addition, the size of such an apparatus would preclude its use where the available space is limited. A solution where effectively multiple spectrometers can be multiplexed in the same available space and the cost does not scale strongly with the field of view would be preferable.

Multiple reflection holograms, multiplexed in a single recording medium, can advantageously be used to reflect each useful spectral line of the analyte to either a single detector or to multiple detectors. However, as the limiting aperture of the optical system becomes an appreciable fraction of the diameter of the collecting lenses or mirrors, it is unavoidable that the holograms will be illuminated with light distributed over a range of angles rather than by perfectly collimated light. The holograms, however, have limited acceptance angle over which they have adequate diffraction efficiency. Hence, the amount of light to be collected will typically scale positively with the acceptance angle of the holograms. The range of angles can be reduced at the expense of using larger diameter optics, but with detrimental effects on cost and size. A large field of view for the holograms can obviate the need for larger optics or, for a given optics size, can increase the amount of light which is collected. It can be readily shown that for plane holograms, the field of view is maximized for near normal incidence illumination with respect to the fringes that comprise the hologram. However, it can be exceptionally awkward to illuminate reflection holograms at near 90° with respect to the surface, for the reflected light will then return substantially along the same path as the illuminating light and the two beams may be difficult to separate.

In addition, it is has been found experimentally that certain scattering processes may produce scattered light which is predominantly polarized. The polarization may be well-preserved, even after passing through a turbid medium (such as human tissue) if the scattered light has not been deflected substantially from its original direction. Inelastic processes such as Raman scattering can provide scattered spectra which contain characteristic spectral signatures of various analytes of interest. If the Raman scattered radiation is collected from a depth within the turbid sample, which is not excessive, it has been found that the scattered radiation is highly polarized.

Fluorescence arising from the excitation of substances which absorb at the exciting laser wavelength is often the dominant source of noise. The fluorescence is generally found to be only weakly polarized, but may be orders of magnitude greater in amplitude than the Raman signals. If a quantitative estimate of the concentration of an analyte is desired, it is desirable to devise an accurate method of subtracting the fluorescence signal from the Raman signal. In addition, it is desirable to preferentially attenuate the fluorescence with respect to the Raman signal in order to improve the signal to noise ratio. It is therefore desirable to find a method whereby the preferential polarization of scattered signals which occurs in some favorable circumstances can be fully exploited to improve signal to noise ratio, and accurately extract the interfering unpolarized radiation.

Approaches to spectroscopy that use dispersive elements such as diffraction gratings suffer from drawbacks. For example, many of these approaches cannot multiplex two or more spectral lines of an analyte onto a single detector for purposes of increasing the signal. Techniques which use cascaded dichroic transmission filters have the same deficiency. Also, neither technique segregates the two polarizations for purposes of subsequent subtraction. The light which is polarized orthogonal to that of the desired signal should be spectrally filtered using filters with substantially the same spectral characteristics that are applied to the first polarization, for otherwise the subtraction of the two signals cannot accurately extract the noise.

Finally, it is frequently desirable to observe the spectral lines of one or more additional analytes in order to accurately establish the absolute concentration of the first analyte. This is particularly true when there are substances present with confounding optical spectra that can overlap the spectrum of the analyte at one or more wavelengths. Each confounding substance, however, may have one or more unique lines different from that of the analyte. Hence, observation of these other lines can be used to extract the contribution of the confounding substances. In a more general approach, a regression algorithm can be constructed to extract the contribution of multiple confounding substances.

Therefore it is desirable to alternatively view additional spectral lines distinct from that of the first analyte. Alternatively, it is often very useful to observe spectral lines of the solvent in which the analyte is dissolved to determine the quantity of the solvent in the scattering volume. Using the volume of solvent, the absolute concentration of the analyte can be determined. Generally observation of many spectral lines has required the implementation of a spectrograph with a linear array of detectors to observe the whole spectrum. This can be expensive when a large detector array is required. Furthermore, the dark current noise of multiple detectors is additive. Hence, the large array may have inferior signal to noise as compared with a smaller array or a single detector.

Thus, there is a need for improved spectroscopic approaches, for example as may be used to detect analytes based on their spectral lines.

BRIEF SUMMARY OF THE INVENTION

These and other limitations are addressed by the present invention, which provides for an optical apparatus in which multiplexed holograms are used to achieve the wavelength selectivity and polarization manipulation is used to facilitate near-normal incidence of light on the holograms. The polarization manipulation allows light reflected from the holograms to be separated from the light incident on the holograms. One benefit of normal incidence is an expanded angular field of view for the holograms. The expanded field of view permits the use of smaller light gathering optics and/or larger apertures within the optical collection system. Larger apertures can be used to increase the size of the scattering volume being imaged, thus increasing the signal produced by the analyte of interest.

In one aspect of the invention, a polarization-sensitive assembly separates the incoming light by polarization. For example, a polarization beam splitter may separate incoming light into orthogonal linear polarizations. The polarization-separated light is incident on one or more holographic assemblies. The holographic assemblies contain multiplexed holograms that reflect light within selected wavelength bands; other light is transmitted. For example, the wavelength bands may be selected based on the spectral lines of an analyte to be detected. The reflected light is separated from the incoming light by the polarization-sensitive assembly, thus allowing normal incidence on the multiplexed holograms.

The apparatus may also include one or more detectors positioned to receive the reflected light. Different polarizations and/or wavelength bands may be routed to different detectors. In one embodiment, all polarizations and all wavelength bands are received by a single detector. In another embodiment, the wavelength bands are divided. Certain wavelength bands are received by one detector, other wavelengths bands by a second detector, and so on. This can be achieved by orienting the corresponding holograms at different angles. In another embodiment, different polarizations are received by different detectors. Combinations of these can also be implemented.

For example, if the desired scattered signal is predominantly polarized in one direction, the signals arising from the orthogonal polarization can be used to subtract the noise arising from unwanted radiation sources which are substantially present in both polarizations. Such unwanted radiation sources may include fluorescence from biological samples. In one implementation, the polarization containing the scattered signal from the analyte is received at one detector and the orthogonal polarization (mostly noise with low to no analyte scatter signal) is received at a separate detector. The two detector signals can then be processed to remove noise from the signal containing the scattered signal from the analyte. In this example, it is desirable for both polarizations to experience the same attenuation when propagating through the system. In one design, the same holographic assembly is used for both polarizations. One polarization is incident on the front side; the other is incident on the back side. In this way, both polarizations will experience the same hologram diffraction efficiency, field of view, etc.

In a specific design, the incident and reflected beams from the holographic assembly are separated by using a quarter-wave plate. The polarization of the incident beam passes through the quarterwave plate and is converted from linear polarization to circular polarization. The beam then reflects off the multiplexed holograms. The reflected beam again passes through the quarterwave plate and is converted from circular to linear polarization, but orthogonal to the incident beam. The difference in polarization is used to separate the two beams.

In yet another aspect of the invention, more than one set of wavelength bands can be interrogated. Different holographic assemblies contain multiplexed holograms that implement different sets of wavelength bands. Thus, one holographic assembly may select wavelength bands based on the spectral lines of a target analyte, another holographic assembly may select wavelength bands based on the spectra lines for some other substance that may be present, and a third holographic assembly may select wavelength bands for the solvent in which the analyte is dissolved. In various designs, the different polarizations can be routed to different combinations of these holographic assemblies and/or the reflected light can be routed to different combinations of detectors. The routings can also vary as a function of time (i.e., time multiplexing).

In one design, all reflected light is routed to a single detector but active polarization rotators change which holographic assemblies are used, thus changing the wavelength composition of the reflected light. In one application, an active polarization rotator is switched between two states. In one state, the analyte wavelengths are routed to a detector. In the other state, the analyte wavelengths plus other wavelengths (e.g., of a confounding substance that partially overlaps with the analyte signal) are routed to the detector. By comparing the two signals, the strength of the analyte and/or the other substance can be determined.

In another aspect of the invention, the system is designed in a modular fashion, using cascadeable stages. The basic design of a stage is modular, allowing additional stages to be added. Thus, one stage may be designed to detect a first set of wavelength bands, but additional stages could be added to detect second, third, etc. sets of wavelength bands.

The methods for routing wavelengths and polarizations of the scattered signals from analytes are equally applicable to the routing of multiple wavelengths and polarizations to different destinations from optical sources, such as lasers. In any particular system, similar techniques can be used to route both source wavelengths and polarizations to different destinations and/or scattered wavelengths and polarizations to different detectors.

Other aspects of the invention include methods and applications corresponding to the devices and systems described above.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

Figure 1:
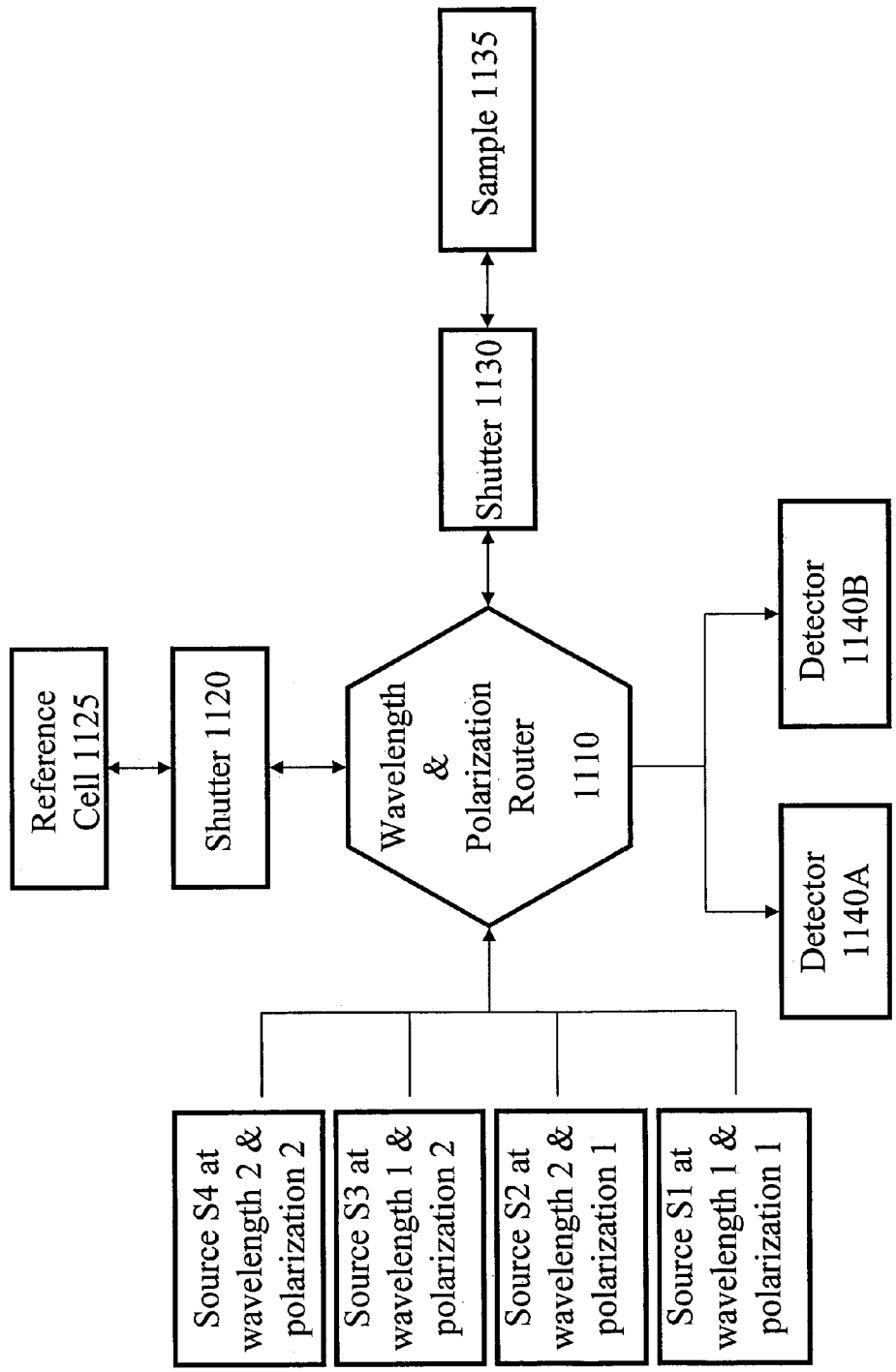
FIG. 1 is a block diagram of a device according to the invention.

FIG. 1 is a high-level block diagram of a device according to the invention, primarily showing the optical functionality of the major components within the device. In this particular example, the device includes four sources S1-S4, two detectors 1140A-B, a reference cell 1125 and shutter 1120, a sample 1135 and shutter 1130, and a wavelength/polarization router 1110.

Generally speaking, the device operates as follows. The sources S1-S4 produce light that is routed by the wavelength/polarization router 1110 to the reference cell 1125 and/or sample 1135 via the respective shutter 1120,130. The shutters 1120,1130 allow time gating of the illumination. Light scattered from the reference cell 1125 and/or sample 1135 is routed by the router 1110 to the detectors 1140.

The sources S1-S4 are shown as having a diversity of wavelengths and polarizations (wavelengths 1-2 and polarizations 1-2 in FIG. 1). The wavelength/polarization router 1110 directs a linear combination of the incident light from the sources S1-S4 via the shutters 1120,130 to the sample 1135 and/or to the reference cell 1125. If $I_{kj}$ is the intensity of the kth source in the jth polarization, then the intensity $I_r$ that illuminates the reference cell 1125 and the intensity $I_s$ that illuminates the sample 1135 are given by:

$$I_r = \sum_{j=1}^{2} \sum_{k=1}^{W} B_{kj} I_{kj} \quad (1)$$

$$I_s = \sum_{j=1}^{2} \sum_{k=1}^{W} A_{kj} I_{kj} \quad (2)$$

respectively, where $0 \leq A_{kj} \leq 1$, $0 \leq B_{kj} \leq 1$, and $A_{kj} + B_{kj} \leq 1$, and W is the total number of sources. The wavelength/polarization router 1110 performs passive power splitting of the incoming light to the different outputs. The coefficients $A_{kj}$ and $B_{kj}$ describe the power splitting that occurs at wavelength k in either of two orthogonal polarizations (j=1 or 2). The specific functionality can be chosen to route substantially all of a given wavelength and/or polarization to either the reference cell 1125 or sample 1135 by designing the wavelength/polarization router 1110 so that the appropriate coefficient is nominally equal to 1 or 0.

Figures 2A, 2B:
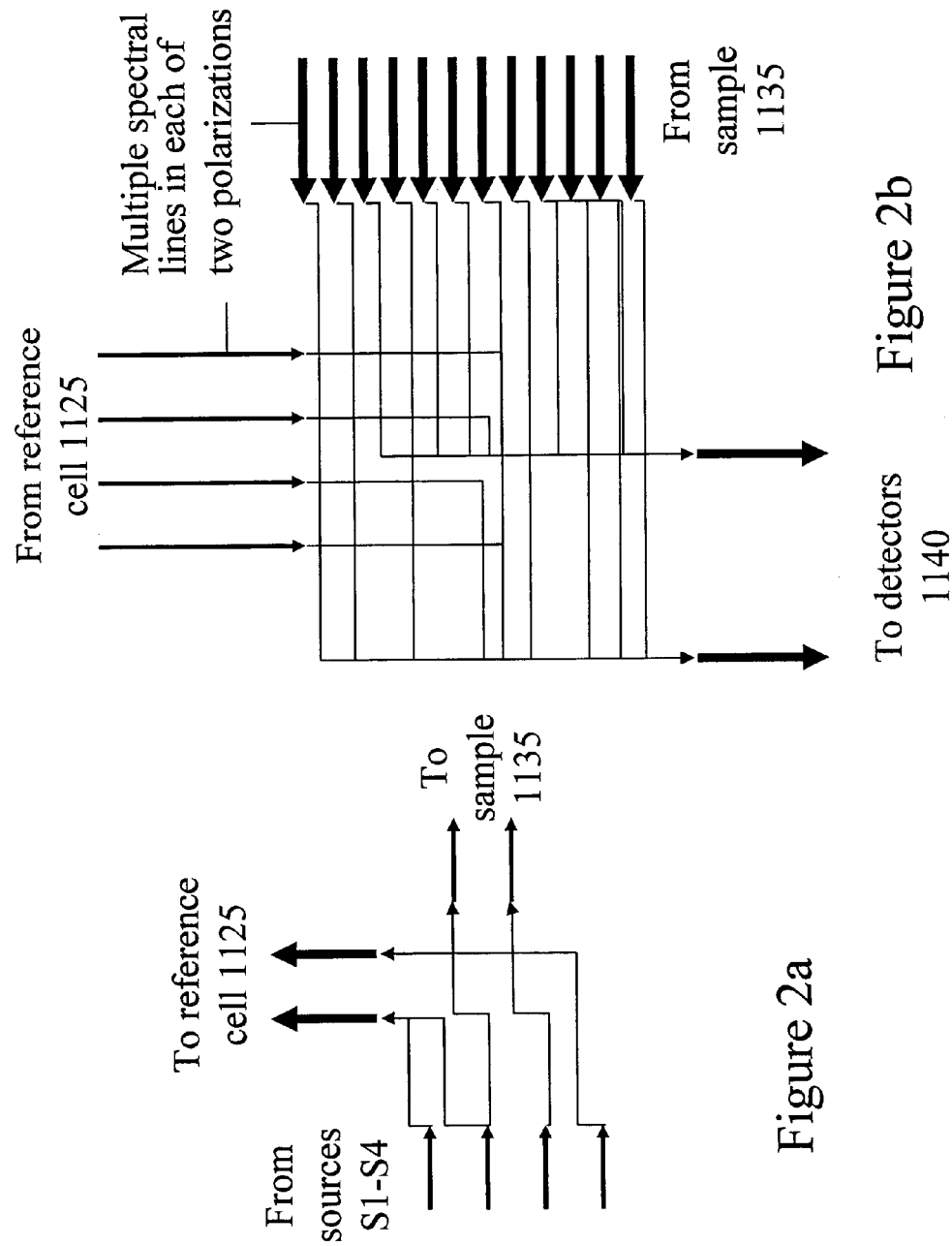
FIGS. 2a and 2b are diagrams illustrating wavelength routing by the wavelength router of FIG. 1.

FIG. 2a is a diagram that shows the wavelength/polarization routing in a pictorial diagram. The four arrows on the lefthand side represent illuminating light produced by the four sources S1-S4. Each arrow represents a specific combination of wavelength and polarization. Each path from a source to a destination (either reference cell 1125 or sample 1135) represents a predetermined fraction of each input wavelength and polarization diverted to the appropriate destination. Light from sources S1, S2 and S4 is routed by the router 1110 to the reference cell 1125. Light from sources S2 and S3 is routed by the router 1110 to the sample 1135. In this diagram, each destination is also represented by arrows; the number of arrows is not meant to have a particular meaning for the destinations. The number of arrows also is not meant to imply characteristics about the physical location or direction of the optical beams. For example, a single arrow does not necessarily correspond to a single physical location or a single incident angle. The corresponding light could be contained in a single optical beam illuminating a single location, or a number of separate optical beams illuminating different locations and/or incident at different angles. In addition, light coming from a source may also be contained in multiple optical beams.

When light from the router 1110 illuminates either the reference cell 1125 or the sample 1135, a scattering signal is generated. The signal typically consists of a multiplicity of spectral lines from the various substances within the reference cell 1125 or the sample 1135. Processes which generate these spectral lines include but are not limited to Raman scattering, second harmonic generation, third harmonic generation, four wave mixing and fluorescence. Any of these processes may produce a spectrum which is characteristic of the analyte to be measured. Each incident wavelength from a source can produce a multiplicity of scattered wavelengths by one or several of the above processes.

Taking Raman scattering as a particularly useful example, each incident wavelength will generate scattered wavelengths at frequencies which are given by the difference of the incident frequency and the characteristic Raman frequencies of the substance. This process is referred to as Stokes Raman scattering. Sum frequency generation also occurs and is referred to as Anti-Stokes Raman scattering.

In the following, the Stokes process is used to illustrate the function of this device but it is not limited to the Stokes process. If there are N incident wavelengths on the sample 1135 and L characteristic Raman frequencies, then the scattered signal will contain N×L=P Raman scattered wavelengths. Each such wavelength may be routed to any of M detectors. As with the routing from source to reference cell/sample, the routing from reference cell/sample to detector is general and can be represented by the equation:

$$I_d = \sum_{j=1}^{2} \sum_{k=1}^{P} C_{dkj} P_{kj} \quad (3)$$

where $I_d$ is the total power incident on the dth detector, $P_{kj}$ is the scattered power at the kth scattered wavelength in the jth polarization, and $C_{dkj}$ is the fraction of the power at the kth wavelength and jth polarization diverted to the dth detector by the router 1110. In the absence of optical amplification, conservation of energy requires that the coefficients $C_{dkj}$ obey the following inequality for any of the individual scattered wavelengths $$\sum_{d=1}^{M} C_{dkj} \leq 1 \quad (4)$$

and where $C_{dkj} \geq 0$ for all values of k and j.

The function of the router 1110 with respect to the scattered wavelengths from the sample 1135 is shown in FIG. 2b, where each path represents the fraction of a given scattered wavelength diverted to a given detector. It is assumed in this example that there are three Raman lines of interest in the sample and the illuminating light is at two different wavelengths and in two different polarizations at each wavelength. Hence, there are a total of 2×2×3=12 scattered Raman signals from the sample. Each arrow on the righthand side represents one of the scattered wavelengths in one of the scattered polarizations. It is assumed that there is one Raman line of interest in the reference cell. Hence, there are four scattered Raman signals from the reference cell.

In many applications, it is preferable that the routing scheme be a non-blocking architecture. The fraction of light that is diverted to a particular destination at a given wavelength and in a given polarization is substantially independent of the fraction of light that is diverted at any other wavelength and any other polarization or to any other destination (subject to conservation of energy, of course). Mathematically, this means that the coefficients $C_{dkj}$ need not be correlated for different values of k and j. Similarly, the coefficients $A_{kj}$ need not be correlated and the coefficients $B_{kj}$ need not be correlated. In many applications, it is also preferable that the architecture also permits broadcasting, which can be defined as the diversion of a fraction of a given wavelength and polarization to more than one destination. The resulting architecture therefore preferably can be a completely general linear non-blocking passive network with broadcast capability.

Further details regarding the operation and features of a similar device, in the context of wavelength routing, are given in pending U.S. patent application Ser. No. 10/923,264, "Measuring Analytes from an Electromagnetic Spectrum Using a Wavelength Router," filed Aug. 20, 2004 by Jan Lipson, which is incorporated by reference herein in its entirety. The following FIGS. 3-9 give further detail on various embodiments for the routing of source and signal wavelengths and polarizations.

The various embodiments presented make substantial use of the manipulation of polarization. In general, it is not necessary to distinguish between linear polarizations which differ by 180°, as there are no physical differences in the operation of the apparatus on polarizations that so differ. In general, polarization may be presented diagrammatically either in a specific direction or a direction 180° from the first direction and both diagrams are equivalent. Similarly, the distinction between left and right hand circularly polarized radiation is not important to the functioning of the apparatus. The operation of birefringent uniaxial crystals such as calcite or quartz can be such as to construct either circular polarization from either linear polarization, and depends on whether these crystals are positive or negative. Such a choice, as long as it is made consistently, does not affect the function of the apparatus.

In many of the following diagrams, both the direction of propagation and the polarization of various optical beams will be shown. The direction of propagation is usually shown as a solid arrow. A solid line with arrowheads on both ends usually indicates two optical beams: one propagating in one direction and another propagating in the opposite direction (e.g., as may be the case upon normally incident reflection from a hologram or mirror). Linear polarization is usually shown as a dashed arrow if in the plane of the paper and by a circle with an x if orthogonal to the plane of the paper. Circular polarization is usually shown by a circle without an x.

Figure 3:
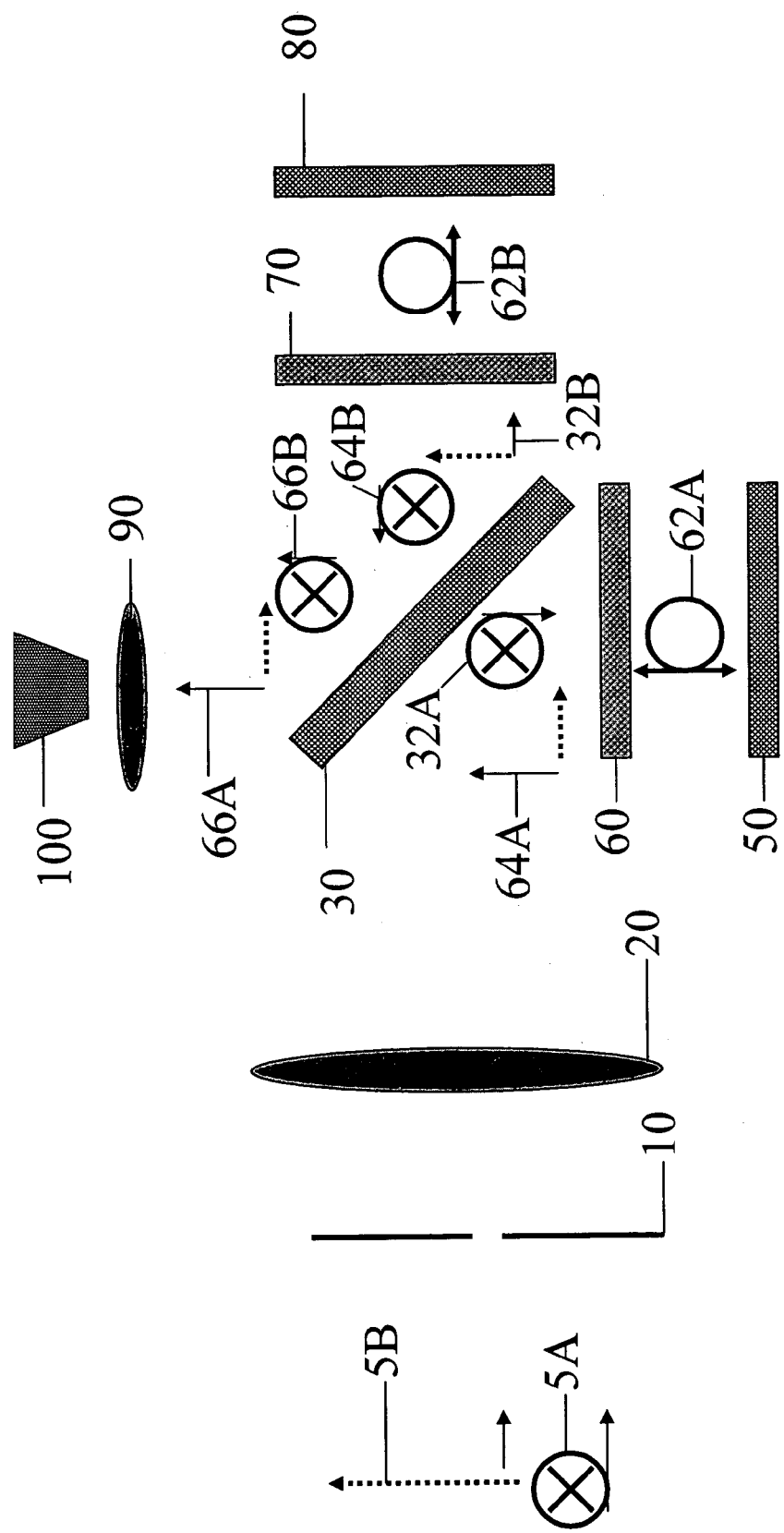
FIG. 3 is a diagram of an optical spectroscopic device according to the invention.

FIG. 3 is a diagram of one embodiment illustrating routing of wavelengths from a sample (not shown) to a detector 100. Scattered light 5 from the sample is imaged by lens 20. The scattered light 5 may contain substantial amounts of radiation in both orthogonal polarizations, as indicated by the dashed arrow 5B and the circle with x 5A. The corresponding solid arrows indicate that the scattered light is propagating from left to right in the figure.

The light 5 is shown as having originated from an aperture 10. The aperture need not be located in the position shown, and need not be a physical aperture. In general, the aperture is defined by the optical element which constrains the size of the scattering volume which is imaged by the optical system. An example of such a possible limiting aperture which is not a physical opening, would be a detector whose diameter is the constraining factor in determining the size of the scattering volume which is imaged upon the detector.

A polarization beam splitter 30 directs the two orthogonal linear polarizations to different directions, shown as optical beams 32A and 32B. The two separate beams of linear polarized light 32A and 32B pass through quarter waveplates 60 and 70, respectively, which transforms the linear polarization to circular polarization, as shown by symbols 62A and 62B. Holographic assemblies 50 and 80, each of which contains a number of multiplexed reflection holograms, reflect the light in selected wavelength bands substantially in the reverse direction (as represented by the return arrowheads in symbols 62A and 62B).

Upon passing through the quarter waveplates a second time, the polarization is converted from circular to linear polarization, as shown by symbols 64A and 64B. However, the linear polarizations of the reflected beams 64A and 64B are orthogonal to the polarization of the original beams 32A and 32B, respectively. When incident upon the polarization beam splitter 30, incident beam 64A passes through as beam 66A, and incident beam 64B is reflected as beam 66B.

Note that while the multiplexed holograms 50 and 80 reflect the optical beam back along the same path, thus allowing normal incidence on the holograms, the polarization manipulation results in an output beam 66 that is not propagating along the same path as the incident beam 5. In FIG. 3, the difference in angle between the input beam 5 and output beam 66 is illustrated as being substantially 90°. However, other angles are possible, for example by choosing a different angular orientation of the polarization beam splitter 30 with respect to the direction of propagation. Beams 66A and 66B have orthogonal polarizations but propagate in the same direction as a result of the operation of polarization beam splitter 30. The composite light 66 is focused onto detector 100 by lens 90.

Figure 4:
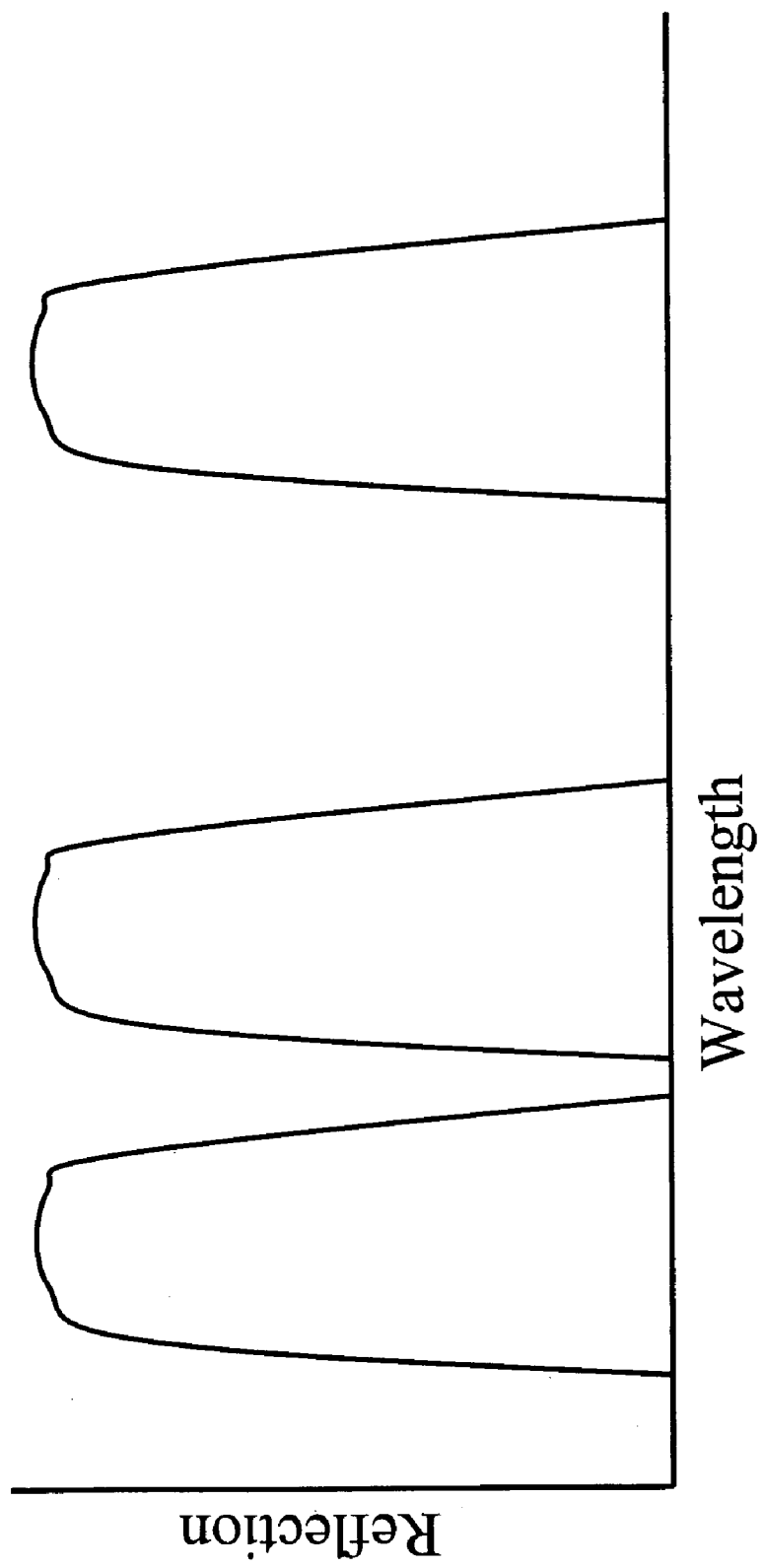
FIG. 4 is a graph of reflectivity as a function of wavelength for the multiplexed reflection holograms.

The operation of the holographic assemblies such as 50 and 80 is illustrated in FIG. 4, which shows qualitatively the functional form of reflectivity as a function of wavelength for these holographic assemblies. Each holographic assembly contains a number of multiplexed reflection holograms, each hologram having a reflection band. Each reflection band is selected preferentially to correspond to a useful spectral line of the analyte or analytes of interest. The width of the reflection band is preferentially selected to be approximately the same as the width of the spectral line of the analyte. The magnitude of the reflectivity is preferentially selected to be near 100%. Further details on the operation and construction of multiplexed holograms is described especially in FIGS. 3, 4 and 6 and the corresponding text of pending U.S. patent application Ser. No. 10/923,264, "Measuring Analytes from an Electromagnetic Spectrum Using a Wavelength Router," filed Aug. 20, 2004 by Jan Lipson, which material is incorporated by reference herein.

Figure 5:
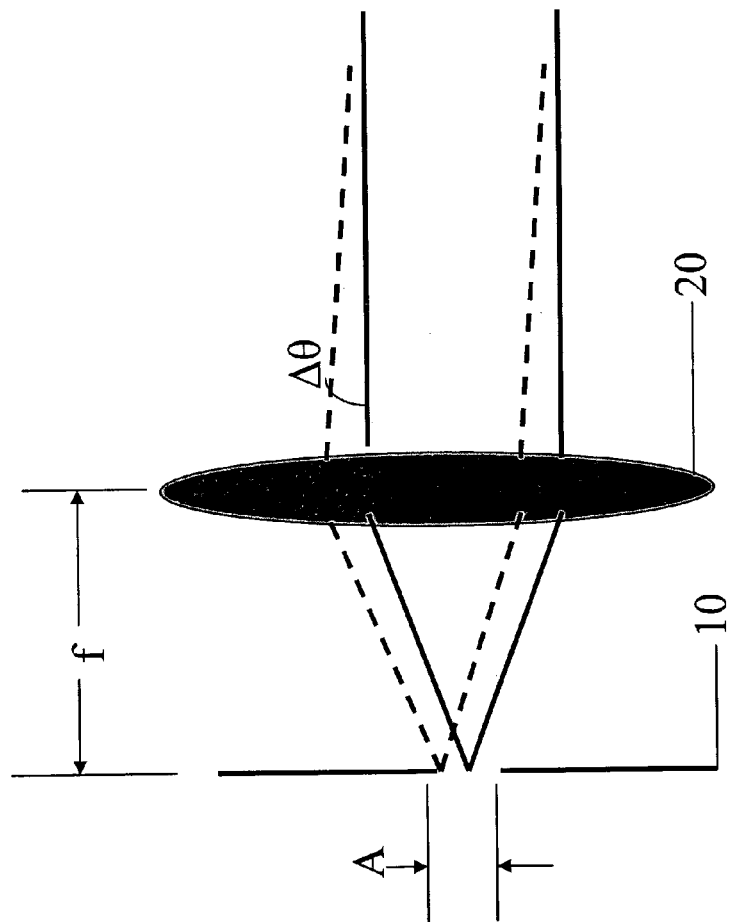
FIG. 5 is a diagram which shows the relationship between the aperture in the optical system and the focal length of the light gathering optic in establishing the field of view.

It is usually desirable to increase the field of view of the multiplexed holograms. When light is collected from the scattering volume by collimating optics of finite size, there will be a distribution in angle of the nominally collimated light. The situation is depicted in FIG. 5 where an aperture of diameter A defines the transverse dimensions of the scattering volume. Light which originates from various points within the aperture is collimated by lens 20. The maximum deviation in angle, $\Delta\theta$, is given approximately by:

$$\Delta\theta = A/2f \quad (5)$$

where f is the focal length of the collimating lens. In order to diffract substantially all the light originating in the aperture, the holograms should have a field of angular view which exceeds $\Delta\theta$. If the field of view is large, then from Eqn. (5) it can be seen that the aperture can be large. The amount of signal that can be collected will scale positively with the size of the limiting aperture of the system. Alternatively, the focal length can be small. For a lens which collects from a fixed solid angle, the diameter of the lenses will scale with the focal length. Accordingly a small focal length lens will have smaller diameter. The cost of optics is a steep function of size. Hence, the reduced diameter of the collection optics can be especially important. Also, some applications are space-constrained, for example where a noninvasive diagnostic instrument must be worn on the body. In these applications, optics size is also especially important.

For holograms, the field of view $\delta$, defined as the angular deviation from optimal angle for which the diffraction efficiency will go to zero, can be obtained by expanding the Bragg diffraction equation to second order in the angular deviation with result:

$$\frac{\Delta\lambda}{\lambda_a} = \cot\theta d\theta - \frac{1}{2} d\theta^2 \quad (6)$$

where, $\theta$ is the angle that the incident light makes with the hologram's fringes, $d\theta$ is the angular deviation from nominal, and $\Delta\lambda$ is the wavelength deviation from the optimal wavelength $\lambda_a$, which causes the diffraction efficiency to go to zero. The field of view is therefore maximized for angles near 90° where the linear term in Eqn. (6) goes to zero. In consequence, it can be seen that the apparatus of FIG. 3 is suitable for increasing the field of view of the holograms because normal incidence is readily achieved, and the retro-reflected light is spatially separated from the incident beam so as to make detection convenient.

Simulations carried out for holograms centered at 830 nm and with bandwidth of 2 nm show that a field of view of approximately 3° half-angle, can be obtained with approximately a 1 nm region of overlapping spectrum where the diffraction efficiency is greater than 80% both for 0° and 3° incidence angles. In this example, the holograms were 1000 μm thick. The maximum refractive index difference of the fringes was 0.003. The background index of refraction was linearly varied over the thickness of the medium by 0.003.

Figure 6:
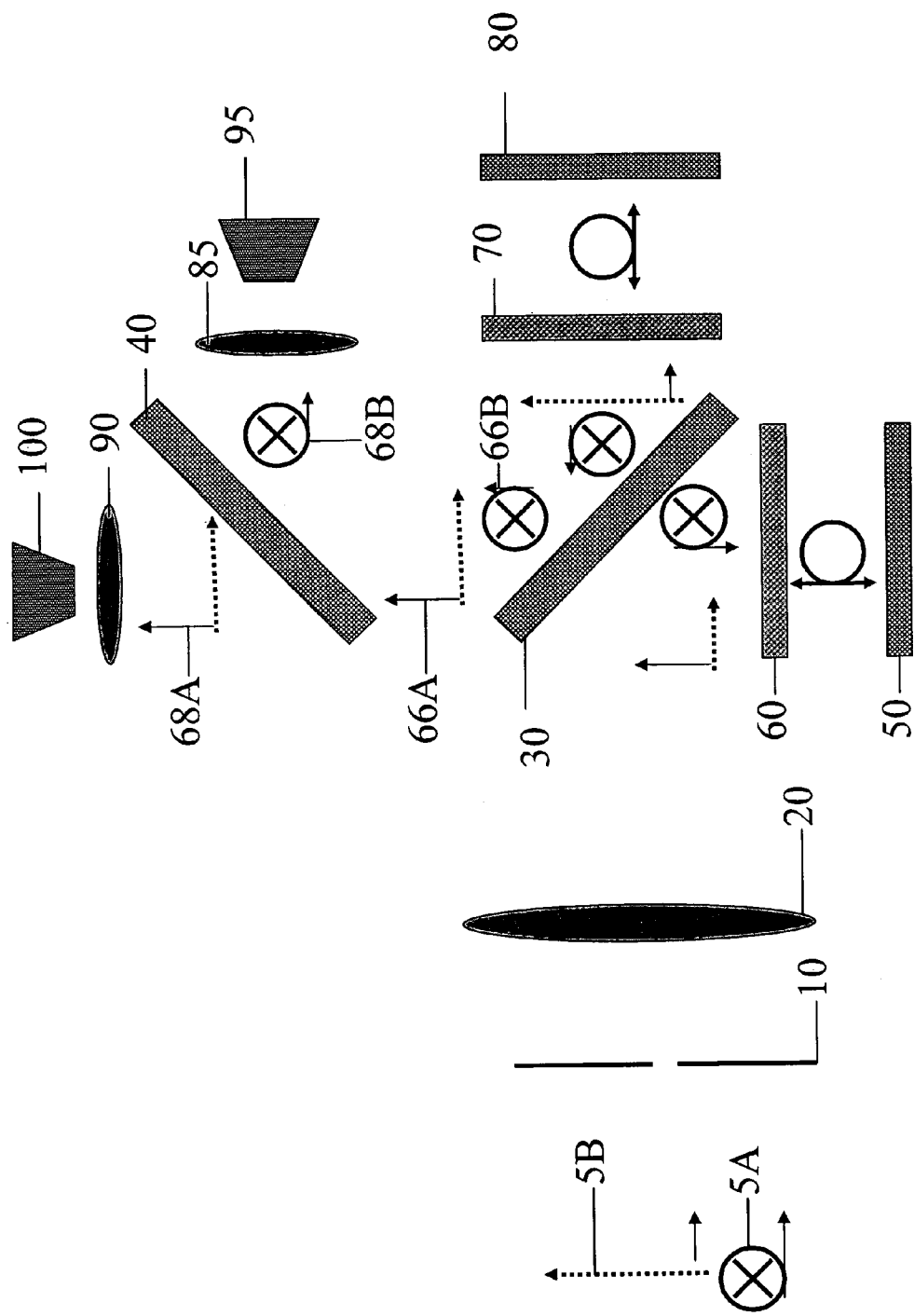
FIG. 6 shows a variation of the optical spectroscopic apparatus of FIG. 3, in which incident radiation in two substantially orthogonal linear polarizations is diverted to two distinct detectors.

An example design suitable for separately monitoring the signals in two orthogonal polarizations is shown in FIG. 6. The apparatus is identical to that of FIG. 3, except that polarization beam splitter 40, lens 85, and detector 95 have been added. In this configuration, one polarization 66A passes through the polarization beam splitter 40 to produce beam 68A, which is collected by detector 100 as before. The other polarization 66B is reflected as beam 68B, which is separately collected by lens 85 and detector 95. Thus, within the wavelength bands of interest, polarization component 5A of the incoming light is routed to detector 100 and polarization component 5B is routed to detector 95.

As a result of the operation of multiplexed holograms, the spectrum of the scattered light is sampled in each of the two orthogonal polarizations. In certain applications, the signal that is desired to be measured is polarized predominantly in one direction and will be substantially detected by one of the two detectors 95, 100. In a preferred embodiment, the multiplexed holograms 50 and 80 are chosen to be substantially identical. The noise is present in both polarizations and hence will be detected by both detectors. If the noise is entirely unpolarized and the signal is entirely polarized, subtraction of the signals emerging from detectors 95 and 100 will extract the noise from the signal. In this ideal example, it is also assumed that all the optics which operate on the two polarizations do so with identical efficiencies and that the detectors have identical responsivity.

In actuality, the noise may not be perfectly unpolarized. In measurements of the polarization properties of human skin, it has been found that the fluorescence noise is split between the two polarizations in the ratio of approximately 47 to 53%. In using the apparatus of FIG. 6, this ratio for the class of samples to be measured can be ascertained as can the optical to electrical transfer characteristics of the apparatus for the two polarizations. Using both the transfer characteristics and the known ratio of polarization for the noise, a scaling factor can be introduced between the signals emerging from detectors 95 and 100 prior to subtraction. The scaling factor is preferentially calculated such that if only noise was present, the difference between the scaled signal from one detector and the actual signal from the other detector would be nominally zero, except for the irreducible variance in the signals being subtracted which will still contribute to the noise. Such a choice will cause the noise to be significantly cancelled upon subtraction when the signal is present, which is a significant benefit. Processing of the two detector signals can be achieved by circuitry, software or other types of conventional logic.

As previously noted, in the designs of FIG. 6, it is preferred to make the multiplexed holograms 50 and 80 identical. One reason is that an accurate subtraction of the noise depends on having the two polarizations subject to preferentially identical spectral filtering. In cases where the noise is very large compared to the signal, small deviations in the spectral filtering characteristics for the holograms encountered by each polarization could give rise to large errors in the estimation of the signal after subtraction. To alleviate this situation, it is advantageous to illuminate a single set of holograms with both orthogonal polarizations, while maintaining the spatial separation of the two polarizations.

Figure 7:
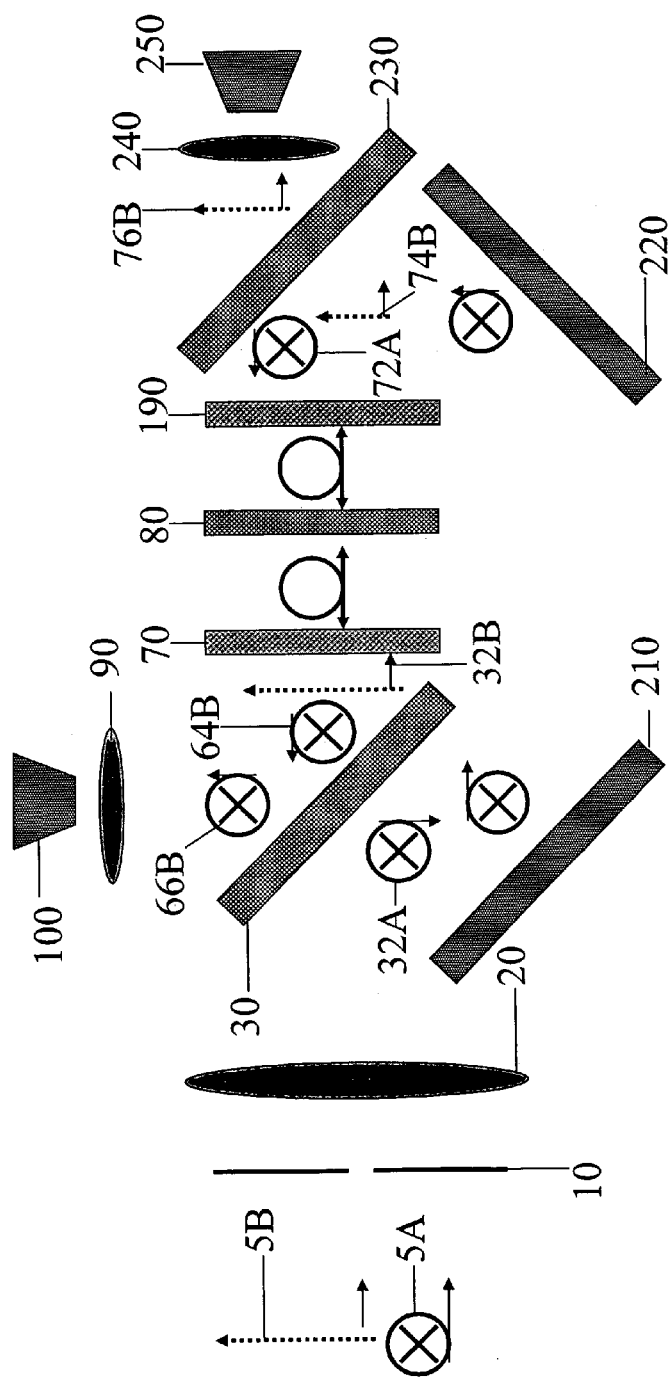
FIG. 7 shows a variation of the optical spectroscopic apparatus of FIG. 3, in which a common holographic assembly is used to diffract both orthogonal linear polarizations.

An alternate optical arrangement using this approach is presented in FIG. 7, where one polarization illuminates the multiplexed holograms from the front and the orthogonal polarization illuminates the multiplexed holograms from the rear. This is accomplished through use of mirrors 210 and 220, in conjunction with polarization beam splitter 230, all of which are configured to divert one polarization so as to be incident on the multiplexed holograms 80 from the direction opposite to that of the orthogonal polarization. The combination of quarter waveplate 190 with holographic assembly 80 accomplishes the same function as the combination of quarter waveplate 70 with holographic assembly 80. The multiplexed holograms 80 will function essentially identically when illuminated from either the front or the rear. Hence, the advantageous objective of creating identical optical transfer functions from the holograms for the two orthogonal polarizations for more accurate subtraction is realized.

In more detail, the polarization component 5B is routed in the same manner as in FIG. 3. Optical beam 5B passes through beam splitter 30, resulting in beam 32B. This passes through wave plate 70, is reflected from holographic assembly 80 and passes back through wave plate 70, resulting in beam 64B. This reflects off beam splitter 30, producing beam 66B which is collected by lens 90 and detector 100.

Polarization component 5A is routed differently to illuminate the opposite side of holographic assembly 80 (rather than a different holographic assembly 50 as in FIG. 3). Reflected beam 32A is routed by mirrors 210 and 220 to polarization beam splitter 230. This incident beam is reflected by the beam splitter 230 towards the back side of the multiplexed holograms 80 (beam 72A). This beam 72A propagates through wave plate 190, is reflected from holographic assembly 80 and passes back through wave plate 190, resulting in beam 74B. Beam 74B is orthogonally polarized relative to beam 72A, so it passes through the polarization beam splitter 230 (beam 76B) and is collected by lens 240 and detector 250.

For the particular case of extracting Raman signals from large background fluorescence, the multiplexed holograms preferably are manufactured with reflection holograms having a reflection-band width in the range 10-100 $cm^{-1}$. In a preferred embodiment, the pass-band widths are selected by matching them to the actual spectral widths of the lines being measured with appropriate allowances for tolerances. For Raman spectroscopy in particular, it is desirable to design holograms with high out of band rejection for the laser wavelength that is used to produce the scattering. That is because Raman scattering is a weak process producing small signals and the stray light from the laser can be large. Rejection of 50 dB is achievable with proper design. In designing the optical system, it is practical to plan on a field of view for the holograms in the range of 0.01 to 0.07 radians for holograms having spectral characteristics suitable for Raman spectroscopy as defined above. The field of view and other relevant performance characteristics are readily modeled using conventional tools such as those described in, "Lipmann-Bragg Holographic Mirrors," T. Jannson et al., Journal of the Optical Society of America, Vol. 8, p. 201 (January 1991).

The proper choice of detector depends on what portion of the optical spectrum is being used, and also on the need for sensitivity. For Raman spectra originating from the scattering of a laser at about 800 nm, it is suitable to choose silicon photodiodes or silicon detectors such as those in CCD arrays.

Quarter waveplates are advantageously obtained from crystalline quartz, and are preferably anti-reflection (AR) coated on both faces. Lenses should also be similarly coated. Polarization beam splitters are conveniently obtained from dichroic multilayer coatings. The surface upon which the polarization beam splitting coating is not deposited is preferably also AR coated.

The devices in FIGS. 3-7 have many commonalities. For example, they all contain some sort of polarization-sensitive assembly that separates the incoming light by polarization and then manipulates the polarization as necessary to achieve the desired routing. In FIG. 3, this is achieved elements 30, 60 and 70; in FIG. 6, by elements 30, 60, 70 and 90; and in FIG. 7, primarily by elements 30, 70, 190 and 230. The entry for the incoming light is to the right of lens 20 in all three figures; the exit is where the outgoing light leaves the polarization-sensitive assembly to be collected by the detector. In addition, in all of these systems, the wavelength selectivity is achieved by a holographic assembly that contains multiplexed holograms, and the wavelength selection occurs after the incoming light has been separated by polarization. Other designs that follow these principles will be apparent.

In many spectroscopic applications it is desirable to measure the spectral lines of multiple substances. In particular, substances whose spectra substantially overlap some of the lines of the target analyte to be measured are often present in the sample. These confounding spectra preferably are properly subtracted to accurately measure the analyte of interest. In many cases, it is possible to find one or more spectral lines for each confounding substance that do not overlap that of the target analyte. The amplitude of these lines then provides a measure of concentration of the confounding substance and may permit accurate subtraction of the spectrum of that substance at each wavelength where there is overlap with the target analyte. A more general algorithm may be developed based on regression in which the best fit to the observed spectrum is derived by finding the concentrations of each substance which when summed best match the data. Alternatively, inverse methods such as principle components regression, or partial least squares regression can be used based on a training set which contains a range of independently measured concentrations. These techniques typically require additional spectral data distinct from the spectrum of the analyte alone.

In addition, a related problem is that of finding the absolute concentration of the analyte when there is not precise knowledge of the sample volume being measured. In some instances, if there is a primary solvent for the analyte, it may be sufficient to measure the spectrum of the solvent. A ratio of the magnitudes of the spectra of analyte and solvent with appropriate scalings based on the different scattering cross-sections may suffice to obtain the absolute concentration of the analyte. Again, however, additional spectral data is required, in this case that of the solvent.

Figure 8:
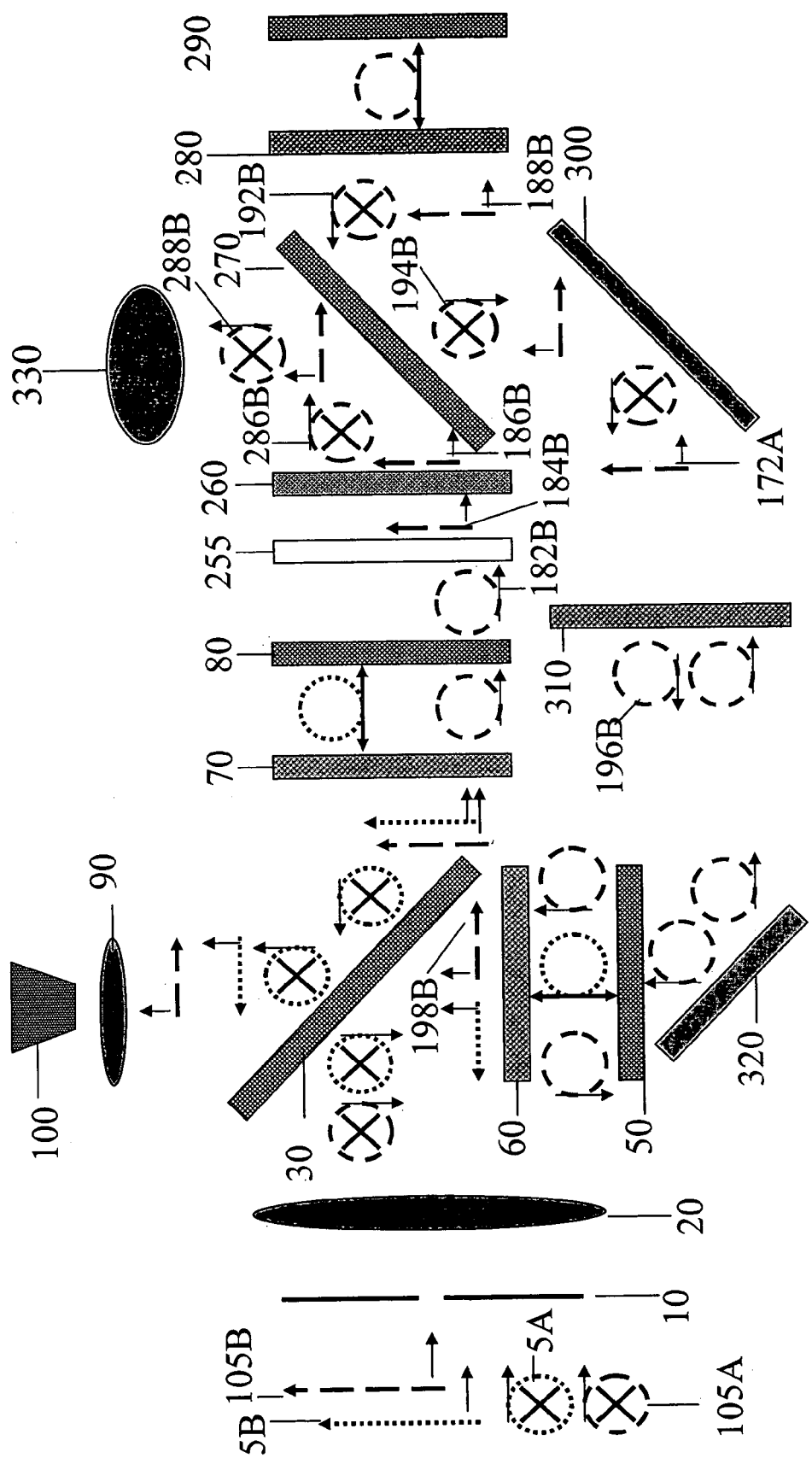
FIG. 8 is a diagram of another optical spectroscopic device according to the invention.
Figure 9:
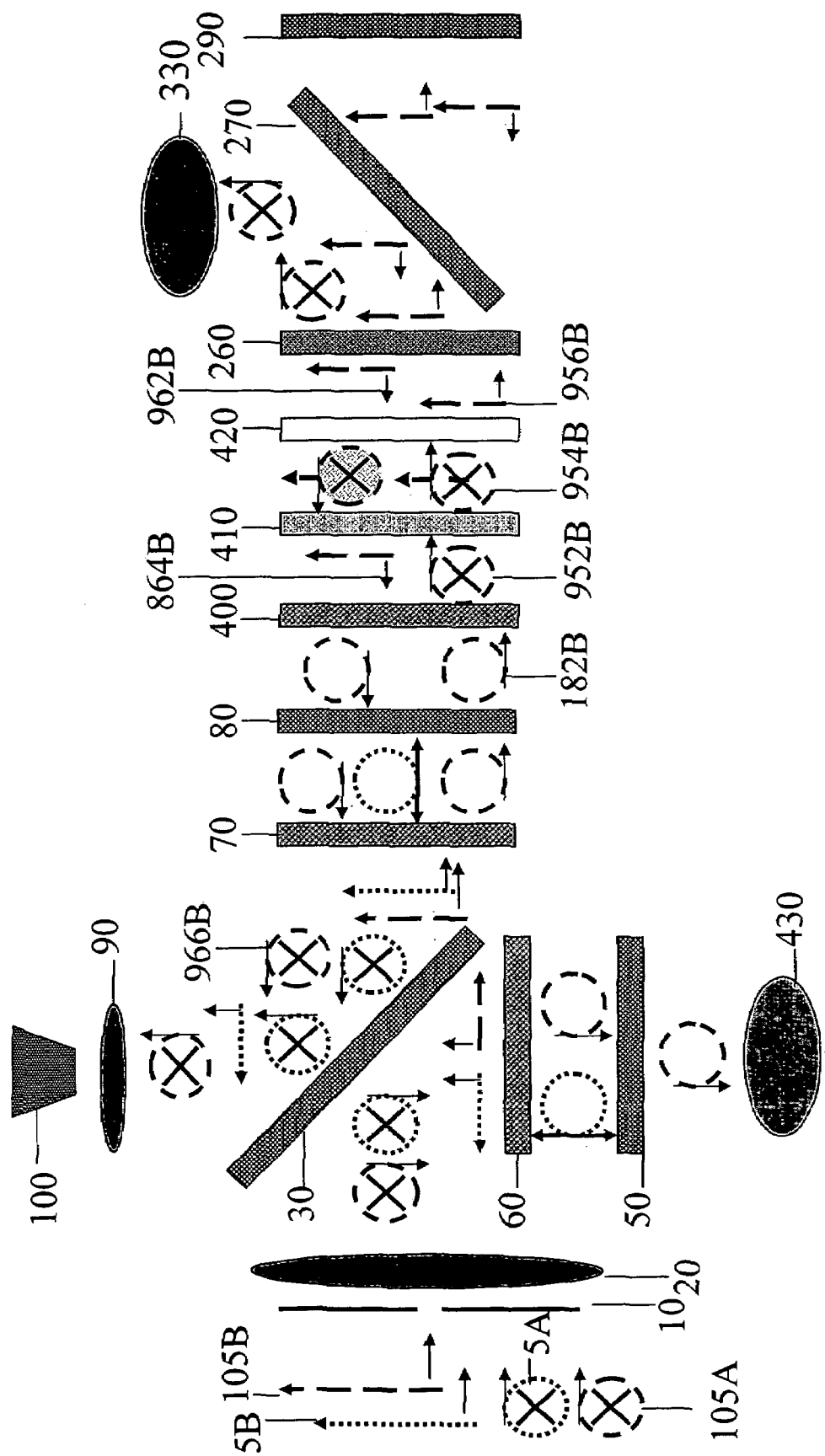
FIG. 9 shows a variation of the optical spectroscopic apparatus of FIG. 8.

FIGS. 8 and 9 show devices that include active polarization rotators. The active polarization rotators switch the device between two different modes. In one mode, the signal in selected wavelength bands is detected. In the other mode, the signal at those wavelength bands plus signal at additional wavelength bands is detected. In the following examples, the wavelength bands that are always present will be referred to as the persistent wavelength bands and the additional wavelength bands will be referred to as the auxiliary wavelength bands.

In one application, the persistent wavelength bands are based on the spectral lines of the target analyte and the auxiliary wavelength bands are based on the spectral lines of some other substance (e.g., the confounding spectra of other substances or the spectra of the solvent). By subtraction of the signals obtained in the two possible states of the device, the summed spectrum of lines distinct from the analyte can be obtained. If the roles of analyte and other substance are reversed, then the summed spectrum for the analyte can be obtained.

Referring to FIG. 8, elements 50 and 80 are holographic assemblies that contain multiplexed holograms. The reflection bands of the multiplexed holograms determine the persistent wavelength bands. Element 290 is another holographic assembly that contains multiplexed holograms, the reflection bands of which determine the auxiliary wavelength bands. Element 260 is the active polarization rotator.

In the following examples, the active polarization rotator 260 is advantageously chosen to be a liquid crystal variable retarder with an integral quarter waveplate and may be procured as an assembly. Faraday rotator 410 is preferably a magneto-optic crystal in a strong magnetic field or in the case of latching materials, with a built in magnetic field. YIG and garnet films are suitable choices. Garnet films can be obtained in latching form obviating the need for a magnet, but are not transparent at all wavelengths of potential interest. YIG is usually suitable if garnet films are not desirable.

In the figures, polarization symbols in short dashes indicate components in the persistent wavelength bands. Polarization symbols in long dashes indicate components in the auxiliary wavelength bands. For example, the incoming light may be unpolarized with both persistent and auxiliary wavelengths. The orthogonal polarization components in the persistent band are represented by 5A and 5B. The orthogonal polarization components in the auxiliary band are represented by 105A and 105B.

With respect to the persistent band, the device in FIG. 8 operates the same as the device in FIG. 3. The physical structure with elements 30, 50, 60, 70, 80, 90 and 100 is the same as in FIG. 3. The incoming light in the persistent band with polarization 5A is routed to detector 100 as follows: reflects off beam splitter 30, passes through quarter waveplate 60, reflects off holographic assembly 50, passes back through quarter waveplate 60 (but with orthogonal polarization), and passes through beam splitter 30 on to detector 100. The incoming light in the persistent band with polarization 5B is routed to detector 100 as follows: passes through beam splitter 30, passes through quarter waveplate 70, reflects off holographic assembly 80, passes back through quarter waveplate 70 (but with orthogonal polarization), and reflects off beam splitter 30 on to detector 100.

The remainder of the device is for handling the auxiliary wavelength bands 105. When the active polarization rotator is off (i.e., no polarization rotation), polarization 105B is routed to the holographic assembly 290, which selectively reflects the auxiliary wavelength band. The reflected light is then routed to the detector 100. When the active polarization rotator is on (i.e., no polarization rotation), component 105B is routed to a beam dump 330. In this example, component 105A is always routed to beam dump 330.

Beginning with polarization 105B, this component will propagate the same as polarization 5B until it reaches the holographic assembly 80. The multiplexed holograms 80 reflect the persistent signal 5B but pass the auxiliary signal 105B as beam 182B. Three-quarter waveplate 255 restores the original linear polarization 184B. Active polarization rotator 260 either leaves the polarization unchanged 186B or, when turned on, rotates the polarization by 90° as indicated by 286B. In this embodiment, the on-state of the active polarization rotator 260 results in the light 286B being reflected from polarization beam splitter 270. The light 288B is then dumped into the beam dump 330.

When the active polarization rotator 260 is in the off-state, the light 186B is passed by device 270. This light 188B passes through quarter waveplate 280. Light in the auxiliary band reflects off multiplexed reflection holograms 290 and passes back through quarter waveplate 280. The resulting light 192B is orthogonally polarized relative to beam 188B. This light 192B is reflected by polarization beam splitter 270. It 194B is reflected by mirror 300 and passes through quarter-waveplate 310, which transforms the polarization to circular 196B. After reflection from mirror 320 and passage through holographic assembly 50, the circular polarization is restored to linear polarization 198B by quarter waveplate 60, with direction orthogonal to the polarization of the light 194B at mirror 300. Polarization beam splitter 30 passes this light, which together with radiation in both polarizations from the persistent band is focused onto detector 100 by lens 90.

For simplicity of illustration, polarization 105A, in this example, is not used. This component is routed to holographic assembly 50 (same as component 5A). The holographic assembly 50 passes the component. The quarter waveplate 60 converts the polarization from circular to linear 172A. The beam splitter 270 passes the light to beam dump 330.

Hence, when the polarization rotator 260 is in the on-state, only the persistent bands 5 are routed to the detector 100. That is, the portion of the apparatus for the auxiliary bands is not activated. When the polarization rotator 260 is in the off-state, the portion of the apparatus for the auxiliary bands is activated and both the persistent bands 5 and the one polarization of the auxiliary band 105B are routed to the detector 100. Therefore, if the signal obtained in the on-state is subtracted from the signal obtained in the off-state, one obtains a difference signal which is the sum of the wavelength components in the auxiliary wavelength band for one polarization. If the persistent band is selected based on the spectral lines of a target analyte and the auxiliary band is selected based on other spectral lines of some other substance, then the difference will be a measure of the other substance. If the measurement times are different for the off- and on-states, a scaling factor which is the ratio of the two measurement times can be introduced prior to subtraction. Other scaling factors can also be used to compensate for other differences in the two measurements.

A great many variations will be obvious from an inspection of FIG. 8. FIG. 9 shows one variant. With respect to component 105B, three-quarter waveplate 255 in FIG. 8 is replaced with the following elements in sequence from left to right: quarter-waveplate 400, non-reciprocal polarization rotator (e.g., a Faraday rotator) 410 which rotates the polarization by 45°, and half waveplate 420 oriented so as to rotate polarization by 45°. Quarter waveplate 280 from FIG. 8 is removed.

The device operates as follows. Quarter waveplate 400 converts circular polarized light 182B to linear polarized light 952B, which is orthogonal to the polarization that is observed for this light just to the left of element 70. Faraday rotator 410 rotates the polarization by 45° (symbol 954B). Half waveplate 420 rotates the polarization by an additional 45° for light traveling from left to right, yielding beam 956B. When device 260 is on, it rotates the polarization and the resulting light is reflected off beam splitter 270 to beam dump 330.

When device 260 is off, the light 956B passes through 270 and is reflected by the holograms of 290, passing back again through device 260, which, in the off position, leaves the polarization unchanged 962B. Device 420 rotates the polarization by −45° for light traveling from right to left since it is a reciprocal device. Device 410, however, being a non-reciprocal device, rotates the polarization by +45°. Hence, the rotations from 420 and 410 cancel for light propagating from right to left, as shown by symbol 964B having the same polarization as 962B. Passage through quarter waveplates 400 and 70 rotate the polarization by 90°, and multiplexed reflection holograms 80 are transparent to this radiation. The light 966B now has the same polarization and direction as the corresponding component from 5B. Polarization beam splitter 30 directs the radiation to lens 90 and thence to detector 100.

In this version, component 105A is routed to a beam dump 430 directly after holographic assembly 50. This is possible because the device has been modified so that component 105B is routed back through holographic assembly 80 to the detector 100, and not via holographic assembly 50 as was the case in FIG. 8.

Multiple additional variants of the configurations of FIGS. 8 and 9 respectively are possible. For example, in FIG. 9, the "arm" to the right of device 80 can be essentially duplicated below device 50 to allow observation of both polarizations 105A and 105B for the incoming light in the auxiliary wavelength. In that embodiment, all four incoming components (5A, 5B, 105A, 105B) would be routed to a single detector 100. In alternate embodiments, different components (or combinations of components) could be routed to different detectors, thus allowing the comparison and/or combination of various signals. A useful variation of this form is to use holographic assemblies with different reflection bands for the two auxiliary arms that emerge from polarization beam splitter 30 (i.e., the arm to the left of holographic assembly 80 and the arm added below holographic assembly 50). This permits the use of two different auxiliary wavelength bands, which can provide additional important data for the extraction of confounding spectra or for calibration.

The architecture in FIG. 9 can also be extended to multiple auxiliary wavelength bands by replicating the structure of 260, 270 and 290 but using different reflection bands for each holographic assembly. Consider each combination of 260, 270 and 290 to be a stage. FIG. 9 then has a single stage. Now replace the beam dump 330 with a second stage that has different reflection bands. If polarization rotator 260 in stage 1 is in the off-state, then the light is routed to holographic assembly 290 of stage 1 and the auxiliary band for stage 1 is implemented. If the polarization rotator 260 in stage 1 is in the on-state, then the light is routed to stage 2. If the polarization rotator 260 in stage 2 is in the off-state, then the light is routed to the holographic assembly 290 of stage 2 and the auxiliary band for stage 2 would be implemented. If the polarization rotator 260 in stage 2 is in the on-state, then the light could be routed to a stage 3, and so on. The resulting device can be used to sample different auxiliary bands on a time-multiplexed basis (i.e., different auxiliary bands sampled by the same detector at different times).

Analogously, the basic design of FIG. 3 could also be cascaded to implement spatial multiplexing (i.e., different bands sampled by different detectors). Wavelengths outside the reflection bands of holographic assembly 80 are passed by the holographic assembly. This can be treated as incoming light (with known polarization) and the basic structure of FIG. 3 can be cascaded to sample a different set of wavelength bands by using holographic assemblies with different reflection bands. The spatial and time multiplexing approaches can also be combined.

As a final example, referring again to FIGS. 8 and 9, holograms 290 and beam dump 330 could be transposed, and holograms 290 can be illuminated when 260 is on rather than when it is off. Further, the role of the holograms for the analyte and for interfering substances could be switched. However, analyte signal is usually at a premium and it is preferable to have the analyte signal traverse the minimum number of optical elements.

Multiplexed reflection holograms can be of arbitrary diffraction efficiency range from 0 too very near unity. It is therefore possible to write a set of multiplexed holograms having a spectrum which can be written as:

$$R(\lambda) = \sum_{i=1}^{N} D_i(\lambda_i) \tag{7}$$

where $R(\lambda)$ is the reflection coefficient at wavelength, $\lambda$, and $D_i(\lambda_i)$ is the reflection coefficient of each hologram which is designed to diffract each of the wavelengths, and N is the total number of lines it is desired to observe.

In many cases an interfering substance has a spectral line distinct from the analyte as well as overlapping spectral lines. Its interference at the observed wavelengths for the analyte are proportional to the strength of the observed signal at the spectral line distinct from the analyte. The constant of proportionality is a fixed property of the substance and can be measured. Therefore by subtracting from the signal a quantity proportional to the light observed at the distinct spectral line of the interfering substance, the interference can be extracted from the analyte signal. If there are multiple interfering substances this operation can be performed for each. The operation can be represented mathematically as follows:

$$S_A = S_M - \Sigma E_k S(\lambda_k) \tag{8}$$

where $S_A$ is the signal arising from the analyte alone, $S_M$ is the measured signal which is the sum of the power from the selected spectral lines of the analyte, but containing interference from other substances, $S(\lambda_k)$ is the signal observed at each of the lines, distinct from those of the analyte, that have been chosen for the interfering substances, and $E_k$ are constants of proportionality which relate the strength of the spectrum in the distinct lines to that of the summed spectra in the lines chosen for the analyte for the interfering substance.

Note that the term to be subtracted in Eqn. (8) is of the same form as that in Eqn. (7). Hence, if the coefficients $D_k$ are related to the coefficients $E_k$ by the relation:

$$D_k = F\ E_k \qquad (9)$$

then a properly weighted measure of the contributions of all the interferers can be obtained directly by choosing the diffraction efficiency of each hologram appropriately. The overall constant of proportionality, F in Eqn. (9) is chosen so that the coefficients $D_k$ can always be <1.0 as is required. It is a fixed number than can be stored in memory and applied to Eqn. (8) as indicated. Note that there is no requirement that only one spectral line for each interferer be selected.

It is possible also to choose the holographic assembly 290 in FIG. 8 or 9 to correspond to advantageous spectral lines of the solvent in which the analyte is dissolved. That permits a straightforward measurement of the quantity of solvent in the scattering volume. The ratio of these signals with that of the analyte yields a correct estimate of the absolute concentration, provided that the ratios of the total scattering cross-sections for the summed lines of the solvent and for the analyte are taken into account through use of a scaling factor.

To create holograms with different diffraction efficiencies it is generally sufficient to vary the exposure time in the writing system for each hologram. The relationship is ideally linear, but saturation effects may be considered if the dynamic range of the material is marginal.

As another example, holograms having different wavelengths of reflection can be disposed at different angles such that the reflected light can be imaged onto different portions of a detector array. This makes it possible to obtain more detailed spectral information that is otherwise possible.

It is also sometimes useful to route polarizations and wavelengths from the sources used to perform scattering to multiple destinations. It is also often desirable to combine the power in two polarizations at the same wavelength and/or to combine wavelengths such as when it is desired to obtain higher levels of signal by illuminating the target with increased optical power, but where individual sources may have less than the desired power. It is also sometimes desirable to make a change in the destinations, to which individual wavelengths and/or polarizations are routed, during the course of the measurement. It is clear from the foregoing that any of the embodiments of FIGS. 3, 6, 7, 8, and 9 and any of their variants can be used to route radiation at multiple wavelengths and polarizations from multiple sources such as lasers. Some examples could include the illumination of more than one target location on the sample, or the illumination of a reference cell which has known concentration of analytes of interest. In the latter case, the scattered signals can provide useful calibration information, enabling an absolute measure of the concentration of one or more analytes. As a final example, a given device may employ these embodiments in combination to route both source and scattered wavelengths and polarizations to desired multiple destinations.

The invention claimed is:

1. An apparatus for routing selected wavelength bands in incoming light comprising:

an entry for receiving incoming light;

a polarization-sensitive assembly positioned to separate the incoming light by polarization;

one or more holographic assemblies containing multiplexed holograms for selectively reflecting the selected wavelength bands of the polarization-separated light; and an exit separate from the entry, where the polarization-sensitive assembly is also positioned to direct the reflected light to the exit.

2. The apparatus of claim 1 in which the angles of incidence of the polarization-separated light upon the multiplexed holograms are in the range of 70-90 degrees with respect to the holographic fringes.

3. The apparatus of claim 1 in which the incoming light is from a sample and the selected wavelength bands are selected based on spectral lines of one or more analytes to be detected.

4. The apparatus of claim 1 in which the incoming light is from one or more optical emitters that produce at least two wavelengths.

5. The apparatus of claim 3 in which a full reflection bandwidth at one-half maximum of at least one of the multiplexed holograms is between 10 and 100 $cm^{-1}$ wavenumbers and lies in the spectral region 250-20,000 nm.

6. The apparatus of claim 3 in which an angular half-field of view at one-half maximum for at least one of the multiplexed holograms is at least 0.01 radians.

7. The apparatus of claim 1 further comprising:

one or more detectors positioned to receive the reflected light from the exit.

8. The apparatus of claim 7 in which the detector(s) consist of a single detector.

9. The apparatus of claim 7 in which the detector(s) comprise an array of detectors.

10. The apparatus of claim 9 in which at least one of the holographic assemblies contains multiplexed holograms disposed at different angles so that light from at least two different selected wavelength bands is reflected to different detectors in the array.

11. The apparatus of claim 7 in which the polarization-sensitive assembly also recombines the reflected light with respect to polarization so that, for at least one wavelength band, incoming light of different polarizations is routed to the same detector.

12. The apparatus of claim 7 in which the polarization-sensitive assembly does not recombine the reflected light with respect to polarization so that, for at least one wavelength band, incoming light of orthogonal polarizations is routed to two different detectors.

13. The apparatus of claim 1 in which, for at least one holographic assembly, incoming light of one polarization is routed to one side of the holographic assembly and incoming light of a different polarization is routed to the other side of the holographic assembly.

14. The apparatus of claim 13 in which the holographic assembly(s) consist of one holographic assembly, and the polarization-sensitive assembly routes incoming light of one polarization to one side of the holographic assembly and routes incoming light of an orthogonal polarization to the other side of the holographic assembly.

15. The apparatus of claim 1 in which the holographic assembly(s) consist of two holographic assemblies, and the polarization-sensitive assembly routes incoming light of one polarization to one holographic assembly and routes incoming light of an orthogonal polarization to the other holographic assembly.

16. The apparatus of claim 1 in which the polarization-sensitive assembly comprises:
a polarization beam splitter to separate the incoming light into a first polarized beam and a second polarized beam having orthogonal linear polarizations; and
for each of the polarized beams: a phase retardation plate that receives the polarized beam and converts said linear polarization of the received polarized beam into a circular polarization and directs the circularly polarized beam to one of the holographic assembly(s), and that also receives the circularly polarized beam reflected back from the holographic assembly and converts the circularly polarized beam to a linear polarization that is substantially orthogonal to said linear polarization of the received polarized beam and directs the linearly polarized beam back to the polarization beam splitter.

17. The apparatus of claim 16 in which the phase retardation plate is a quarter waveplate.

18. The apparatus of claim 1 further comprising:
an entry for a second stage for receiving light transmitted by at least one of the holographic assembly(s);
one or more holographic assemblies for the second stage containing second multiplexed holograms for selectively reflecting second, different selected wavelength bands of the received light;
an exit for the second stage that is separate from the entry for the second stage; and
a polarization-sensitive assembly for the second stage positioned to route the received light from the entry of the second stage to the holographic assembly(s) of the second stage, to the exit of the second stage.

19. An apparatus for routing selected wavelength bands in incoming light comprising:
a polarization-sensitive assembly positioned to separate incoming light by polarization;
one or more holographic assemblies containing multiplexed holograms for selectively reflecting the selected wavelength bands of the polarization-separated light; and
where the polarization-sensitive assembly is also positioned to direct the reflected light in two or more different directions so that incoming light of different polarizations is routed to different directions.

20. The apparatus of claim 19 in which the angles of incidence of the polarization-separated light upon the multiplexed holograms are in the range of 70-90 degrees with respect to the holographic fringes.

21. The apparatus of claim 19 further comprising:
two or more detectors positioned to receive the reflected light routed to different directions.

22. The apparatus of claim 21 in which the incoming light is from a sample and the selected wavelength bands are selected based on spectral lines of one or more analytes to be detected.

23. The apparatus of claim 22 further comprising:
logic for combining detector signals from said different detectors to which incoming light of different polarizations is routed.

24. The apparatus of claim 22 further comprising:
logic for combining detector signals from a first detector and a second detector, where the polarization-sensitive assembly separates the incoming light into two orthogonal linear polarizations and routes light of one linear polarization to the first detector and routes light of the other linear polarization to the second detector.

25. The apparatus of claim 24 in which combining the detector signals reduces noise.

26. The apparatus of claim 24 in which the logic calculates a difference based on the two detector signals.

27. The apparatus of claim 24 in which the logic scales the detector signals and calculates a difference of the scaled detector signals.

28. The apparatus of claim 24 in which the incoming light is from a sample; the selected wavelength bands are selected based on spectral lines of one or more analytes to be detected; the incoming light from the analytes is predominantly polarized along a first linear polarization that is directed to the first detector; noise is predominantly unpolarized; and the logic scales the detector signals and calculates a difference of the scaled detector signals.

29. The apparatus of claim 24 in which the holographic assembly(s) consist of one holographic assembly, and the polarization-sensitive assembly routes incoming light of one linear polarization to one side of the holographic assembly and routes incoming light of the other linear polarization to the other side of the holographic assembly.

30. The apparatus of claim 24 in which the polarization-sensitive assembly comprises:
a polarization beam splitter to separate the incoming light into the two orthogonal linear polarizations; and
for each of the two linear polarized beams: a phase retardation plate that receives the polarized beam and converts said linear polarization of the received polarized beam into a circular polarization and directs the circularly polarized beam to one of the holographic assembly(s), and that also receives the circularly polarized beam reflected back from the holographic assembly and converts the circularly polarized beam to a linear polarization that is substantially orthogonal to said linear polarization of the received polarized beam and directs the linearly polarized beam back to the polarization beam splitter.

31. The apparatus of claim 19 in which the incoming light is from one or more optical emitters that produce two distinct polarizations.

32. An apparatus for routing selected wavelength bands in incoming light comprising:
a first stage comprising:
a first entry for receiving incoming light;
a first polarization-sensitive assembly positioned to separate the incoming light by polarization;
one or more first holographic assemblies containing first multiplexed holograms for selectively reflecting first selected wavelength bands of the polarization-separated light;
a first exit, where the first polarization-sensitive assembly is also positioned to direct light reflected from the first holographic assembly(s) to the first exit; and
a second stage comprising:
a second entry for receiving light transmitted by at least one of the first holographic assembly(s);
one or more second holographic assemblies containing second multiplexed holograms for selectively reflecting second selected wavelength bands of the received light, where the second selected wavelength bands are different from the first selected wavelength bands;
a second exit; and
an active polarization rotator that can be switched between activating and not activating the second stage, where activating the second stage results in routing the received light to the second holographic assembly(s) and then to the second exit.

33. The apparatus of claim 32 further comprising:
one or more detectors positioned to receive the reflected light from the first exit, where light routed by the active polarization rotator to the second exit will propagate to the same detector(s) via the first exit.

34. The apparatus of claim 32 further comprising:
one or more first detectors positioned to receive the reflected light from the first exit; and
one or more second detectors separate from the first detector(s), positioned to receive light routed by the active polarization rotator to the second exit.

35. The apparatus of claim 32 further comprising:
one or more detectors positioned to receive light from the first exit and/or the second exit when the second stage is activated and when the second stage is not activated.

36. The apparatus of claim 35 in which the detector(s) are spatially multiplexed to receive light when the second stage is activated and when the second stage is not activated.

37. The apparatus of claim 35 in which the detector(s) are time multiplexed to receive light when the second stage is activated and when the second stage is not activated.

38. The apparatus of claim 35 further comprising:
logic for combining a detector signal from the detector(s) when the second stage is activated and a detector signal from the detector(s) when the second stage is not activated.

39. The apparatus of claim 38 in which combining the detector signals reduces noise.

40. The apparatus of claim 38 in which the logic calculates a difference based on the detector signals.

41. The apparatus of claim 38 in which the logic scales the detector signals and calculates a difference of the scaled detector signals.

42. The apparatus of claim 38 in which the detector signal for the not activated second stage is based on spectral lines of one or more analytes to be detected; and the detector signal for the activated second stage is based on spectral lines of the analyte(s) to be detected and spectral lines of one or more other substances.

43. The apparatus of claim 38 in which the detector signal for the not activated second stage is based on spectral lines of one or more analytes to be detected; and the detector signal for the activated second stage is based on spectral lines of the analyte(s) to be detected and spectral lines of a solvent in which the analyte(s) are dissolved.

44. The apparatus of claim 32 in which the first polarization-sensitive assembly separates the incoming light into two orthogonal linear polarizations and the active polarization rotator routes only one of the polarizations to the second exit.

45. The apparatus of claim 32 in which the active polarization rotator is based on polarization rotation in liquid crystals.

46. The apparatus of claim 32 further comprising:
a third stage comprising:
a third entry for receiving light from the second stage when the second stage is not activated;
one or more third holographic assemblies containing third multiplexed holograms for selectively reflecting third selected wavelength bands of the received light, where the third selected wavelength bands are different from the first and second selected wavelength bands;
a third exit; and
an active polarization rotator that can be switched between activating and not activating the third stage, where activating the third stage results in routing the received light to the third holographic assembly(s) and then to the third exit.

47. The apparatus of claim 32 in which the incoming light is from one or more optical emitters that produce at least two wavelengths.

48. The apparatus of claim 32 in which the incoming light is from one or more optical emitters that produce distinct polarizations.

49. The apparatus of claim 32 in which the second stage further comprises:
a non-reciprocal polarization rotator that rotates polarization of light propagating in one direction by 90 degrees differently than light propagating in an opposite direction.

* * * * *